United States Patent [19]

Weldon et al.

[11] Patent Number: 5,084,065
[45] Date of Patent: Jan. 28, 1992

[54] REINFORCED GRAFT ASSEMBLY
[75] Inventors: Norman R. Weldon; David C. MacGregor, both of Miami, Fla.
[73] Assignee: Corvita Corporation, Miami, Fla.
[21] Appl. No.: 377,463
[22] Filed: Jul. 10, 1989
[51] Int. Cl.$^5$ ............................ A61F 2/06; A61F 2/04
[52] U.S. Cl. ......................................... 623/1; 623/12; 600/37; 606/156
[58] Field of Search ................. 623/1, 11, 12; 600/37; 606/153, 156

[56] References Cited

U.S. PATENT DOCUMENTS

| | | |
|---|---|---|
| 3,187,752 | 6/1965 | Glick . |
| 3,479,670 | 11/1969 | Medell ................................. 623/12 |
| 3,490,975 | 1/1970 | Lightwood . |
| 3,688,317 | 9/1972 | Kurtz ..................................... 623/1 |
| 4,130,904 | 12/1978 | Whalen . |
| 4,355,426 | 10/1982 | MacGregor . |
| 4,475,972 | 10/1984 | Wong . |
| 4,629,458 | 12/1986 | Pinchuk . |
| 4,743,252 | 5/1988 | Martin, Jr. et al. . |
| 4,850,999 | 7/1989 | Plank ..................................... 623/1 |
| 4,857,069 | 8/1989 | Kira ....................................... 623/1 |

Primary Examiner—Randall L. Green
Assistant Examiner—Paul Prebilic
Attorney, Agent, or Firm—Lockwood, Alex, FitzGibbon & Cummings

[57] ABSTRACT

A reinforced graft assembly made from a vascular graft component and a reinforcing sleeve component. The reinforcing sleeve component may include one or more layers. The diameter of the inner surface of the most internal layer of the reinforcing sleeve component is approximately equal to or larger than the diameter of the vascular graft component thereby allowing the former to be fitted over the latter. The compliance of the sleeve component is adjustable depending on the application needs, for example, by varying the angle at which the fibers used to form the sleeve component are laid down and by the method used to join the two components.

11 Claims, 1 Drawing Sheet

REINFORCED GRAFT ASSEMBLY

BACKGROUND AND DESCRIPTION OF THE INVENTION

The present invention generally relates to a graft. More particularly, the invention relates to a graft, such as a vascular graft, constructed from two components: a synthetic, biologic or biosynthetic vascular graft component and a reinforcing sleeve component, each of which has an appropriately sized internal diameter so the graft component may be fitted within the sleeve component.

In the medical treatment of patients with diseased arteries or veins, surgeons may replace the failing tissue with prosthetic conduits such as vascular grafts. Conventional grafts, however, can kink or collapse mechanically under a variety of circumstances such as when the graft is bent during the contraction of the surrounding muscle, or when external pressure is applied to the graft during a period of rest taken by the recipient of the graft. One conventional solution to these problems has consisted of the reinforcement of the walls of vascular grafts by the weak attachment of either discrete polymeric rings or continuous spiral polymeric bands to a portion, albeit often a small portion, of the exterior surface of the prosthesis.

Grafts to which such limited reinforcing rings or bands are attached have certain limitations. One limitation of conventionally reinforced vascular grafts is that the reinforcing member may interfere with the creation of an anastomosis. In such a case, the reinforcement must be physically removed by peeling or cutting it off the graft at the time of surgery. Another limitation is that, because the reinforcement is confined to certain areas of the graft, the reinforcement may not necessarily coincide with the area where the reinforcement protection is actually needed. This may happen where the most desirable site to create the proximal and distal anastomosis is in an area of the patient which anatomically presents difficulties to the placement of the reinforced graft. An additional limitation is that the stiffness of the reinforcing member may reduce the circumferential and/or longitudinal compliance of the graft. A non-compliant graft will reduce the pulsatile flow through the graft thereby compromising the ability of the prosthesis to perform naturally. Fourth, the reinforcing members of conventional vascular grafts have a smooth and non-porous surface. Such a surface cannot be penetrated by cellular growth and, accordingly, represents a biologically incompatible interface between the graft and the host tissue. This incompatibility may cause the erosion of the surrounding tissue, the formation of undesirable bursae and fibrotic capsules, or the formation of calcium deposits.

The present invention includes a two-component system, one component of which, the graft component, comprises a synthetic, biologic or biosynthetic graft, including the type detailed in U.S. Pat. No. 4,355,426 to MacGregor and, in part, in U.S. Pat. No. 4,743,252 to Martin and MacGregor and fabricated in the manner detailed in U.S. Pat. No. 4,475,972 to Wong. These patents are incorporated by reference hereinto. The other component, the sleeve component may be formed from synthetic, biologic, or biosynthetic material. The graft component comprises a porous surface and a network of interconnected interstitial pores below the surface, which network is in fluid flow communication with the surface pores.

The second component of the two-component system of the present invention includes a reinforcing sleeve component. Like the graft component, the second component includes a porous surface and a porous subsurface. The sleeve component has an internal diameter that is equal to or larger than the external diameter of the graft component and, as such is sized so that it may be fitted over the first component of the present invention.

The two-component system of the present invention provides advantageously a system which, while providing reinforcement to a graft, overcomes the limitations associated with conventional graft reinforcement systems. For example, by separating the graft component from the reinforcing sleeve component, the blood transporting function handled by the former is isolated from the mechanical load bearing function handled by the latter. This isolation acts to preserve the inherent compliance of the blood transporting member. A non-compliant blood transporting member will interfere with and break up the natural wave flow of in vivo blood, which is a serious disadvantage of prior art reinforced grafts. Generally speaking, prior art reinforced vascular grafts can reduce the pulsatile flow of blood therethrough by a factor of some 10 to 30 percent.

The two-component system of the present invention also allows the separate reinforcing sleeve component to be located at any position along the length of the prosthesis or even across an anastomosis thereby providing support to a localized section of the graft or host artery. For example, during the course of surgery, the slidable reinforcing sleeve according to this invention can be precisely located to provide needed reinforcement at a precise location, such as across a knee joint, a rib cage or the like.

A two-component system, as in the present invention, in which the graft component is reinforced by a sleeve component, also may be fitted into a restricted area without requiring the removal of the segmented reinforcing rings or bands taught in conventional reinforced vascular grafts. Additionally, because the reinforcing sleeve component may be fixed over the graft component through a variety of means, and the means chosen to accomplish the fixation affects to a certain degree the compliance, the resultant compliance of the reinforced graft assembly is adjustable. In addition, compliance is adjustable by winding the fibers of the reinforcing sleeve component at an angle which enhances kink resistance. Compliance is also adjustable by varying the durometer hardness of the fibers from which the reinforcing sleeve component is made.

The structure of the present invention aids in rendering the invention biocompatible and hemocompatible and facilitates its fixation within the body. The former advantage is realized due to the porous surface and subsurface network characterizing the structure of the invention. This structure encourages cellular ingrowth and allows a smooth, thin tissue coating to form and to adhere to the porous surface of the present invention. Desirably, this coating renders the graft resistant to the formation of blood clots which are normally associated with the presence of foreign bodies such as grafts or prostheses, in the blood stream. The latter phenomenon, that is, the fixation of the strengthened graft to the adjacent tissues, is caused also by the formation of the adherent tissue coating on the porous surface. It allows the implant to be incorporated into the cardiovascular system thereby achieving a more secure attachment than previously obtainable.

It is, accordingly, a general object of the present invention to provide an improved graft.

Another object of the present invention is to provide an improved graft assembly having a compliant inner graft component and a reinforcing sleeve component that does not substantially interfere with the compliant properties of the inner graft component.

Additionally, it is an object of this invention to provide an improved reinforced graft whose overall compliance is adjustable.

Another object of this invention is to provide an improved reinforced graft and method of making same.

These and other objects, features and advantages of this invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
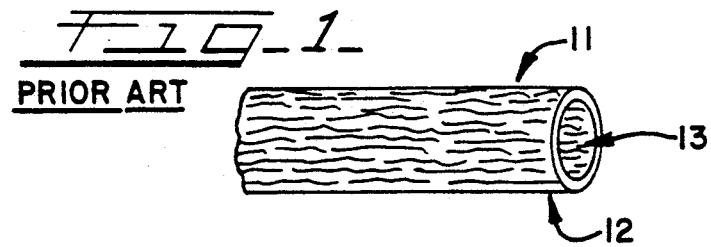
FIG. 1 is a perspective view, partially broken away, of a known graft component suitable for inclusion in the assembly according to the present invention.

The present invention typically is a two-component assembly of a synthetic, biologic or biosynthetic graft component of generally known type together with an external reinforcing sleeve component. The graft illustrated in the drawings is a vascular graft component.

The preferred graft component is illustrated in FIG. 1 and is generally designated by reference numeral 11. Graft component 11 has a porous surface 12 and a network 13 of interconnected interstitial pores below the surface which are in fluid flow communication with the surface 12. When the device is implanted, the porous surface 12 and the subsurface network 13 promote cellular ingrowth and the formation of a smooth, thin, adherent tissue coating, not shown, on the porous surface 12. This coating renders the graft component 11 biocompatible and hemocompatible and specifically allows the surface 12 to remain resistant to the formation of blood clots and the like normally associated with the presence of foreign bodies, such as grafts or prostheses, in the blood stream. Additionally, the coating facilitates a secure attachment of the graft into the cardiovascular system.

The methods by which the graft component 11 may be fabricated include those disclosed in U.S. Pat. No. 4,475,972. In one fabrication method disclosed in U.S. Pat. No. 4,475,972, and termed "solution processing", a biocompatible polymeric material, such as biocompatible polyurethane, is dissolved in a suitable solvent, such as dimethyl formamide, to form a viscous solution. The resultant "wet" solution is pumped under pressure into a distributor and out through one or more orifices to form one or more continuous filaments of tubular material. The extruded fiber or fibers are placed in contact with a rotating mandrel. Because the exterior diameter size of the mandrel will determine the inner diameter size of the graft component 11, a graft of almost any internal diameter size may be made by choosing a mandrel of the appropriate size. The distributor or spinnerette reciprocates from one axial end of the mandrel to the other so that the fibers are wound onto the mandrel in different and opposite directions.

The conditions of the winding process are critical for purposes of optimizing those characteristics which directly affect the performance of the graft component 11. One such characteristic is the compliance of the graft component 11. This characteristic may be varied by selecting the appropriate diameter of the fiber from which the graft component 11 is formed. The circumferential speed of the rotating mandrel will determine to what degree the fiber extruded in contact with the mandrel will stretch. The greater the stretch, the smaller the diameter of the fiber and the greater the flexibility and compliance of the resultant graft. Compliance may also be varied according to the angle at which the fiber used to form the graft component 11 is wound. Radial compliance varies on an inverse proportional basis to the angle of winding, with a less compliant graft made by increasing the angle of winding, defined as an acute angle with respect to the axis of the graft or mandrel on which it is wound.

"Kink resistance", that is, the ability of the graft to be bent without greatly reducing the cross-sectional area of the inside of the graft, is another characteristic which may be varied by the angle at which the fiber forming the graft component 11 is wound. A graft with little "kink resistance" will kink with only little bending of the graft thereby stopping the flow of blood. The larger the angle of winding, the greater the ability of the graft to withstand flexing without kinking, and the more useful the graft is for application in locations which may be subjected to such flexing.

The porosity and the shape of the pores of the graft depends also on the angle at which the fiber is wound onto the mandrel. Specifically, a smaller angle of winding will produce a smaller pore size and reduced porosity. The spinnerette is allowed to reciprocate with respect to the mandrel until the desired thickness of overlayed filaments is obtained. When desired, the filaments may be extruded from the mandrel "wet", and upon evaporation of the solvent, the filaments securely bond to each other at the point of overlap. A stable and nonwoven structure results without the need for additional processing.

While spinnable polyurethane materials are preferred, the graft may also be made from other polymeric materials, such as polyolefins including polyethylene. With such polymeric materials, the spinnerette may be heated to produce tacky, fusible, and substantially solvent-free fibers which bond to each other on the mandrel as the fibers cool. Alternatively, the mandrel may be heated to fuse fibers as they are laid on each other.

The reinforcing sleeve component according to the present invention is illustrated in FIG. 2 through FIG. 6. This component includes one or more layers which form a sleeve that is suitable for fitting over the graft component of the graft assembly according to the invention.

Figure 2:
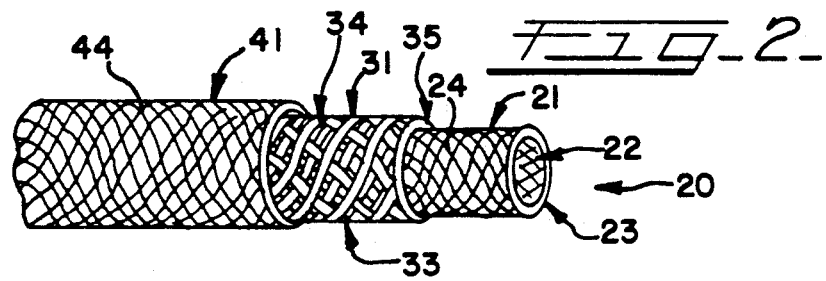
FIG. 2 is a perspective view, partially cut away, of one embodiment of a reinforcing sleeve component according to this invention into which the graft component illustrated in FIG. 1 may be fitted.

One embodiment of the reinforcing sleeve component according to the present invention, designated 20 in FIG. 2, includes three layers: a first or internal layer 21; a second or intermediate layer 31; and a third or external layer 41. The internal layer 21 may be formed from synthetic, biologic, or biosynthetic and generally biocompatible material according to the method taught in U.S. Pat. No. 4,475,972 (as generally described above) and from fibers 24 which may range from about 1 micron to about 100 microns and preferably from 5 to 30 microns in diameter. The resultant internal layer 21 has an inner cylindrical surface 22 whose diameter is equal to or greater than the exterior diameter of the mandrel, not shown, on which the internal layer 21 is formed.

Onto the outer cylindrical surface 23 of the internal layer 21, an intermediate layer 31 may be wound. The intermediate layer may be formed from fibers of a biocompatible material according to the method taught in U.S. Pat. No. 4,475,972. Preferably, the fibers are in the shape of a ribbon or filament 34 which is generally flat or rectangular in cross section, thereby enhancing the stiffness of the sleeve component 20. The fibers of this intermediate layer 21 could be generally circular, depending upon the particular stiffness properties that are needed for the sleeve component 20. The ribbon or filament 34 is wound at an angle ranging from 35° to 85° with respect to the common longitudinal axis of the reinforced vascular graft 20 and may have a diameter which may range in size from 300 to 3,000 microns and preferably 500 to 1,000 microns.

An external layer 41 may be fabricated and laid over the outer surface 33 of the intermediate layer 31 according to the methods disclosed in U.S. Pat. No. 4,475,972 and as discussed above. Biocompatible material in the form of fibers 44, 1 micron to 100 microns and preferably 5 to 30 microns in diameter may be used to make the external layer 44.

Figure 4:
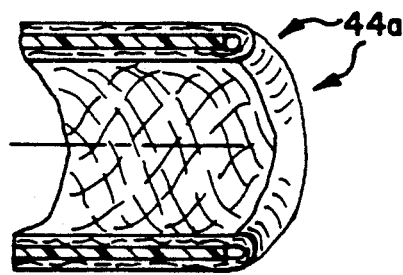
FIG. 4 is a cut away perspective view illustrating a cross-section of the reinforcing sleeve component shown in FIG. 2 in which the component is protected from biodegration by spinning the fibers which form the internal layer and the external layer beyond the intermediate layer ribbon or filament.
Figure 5:
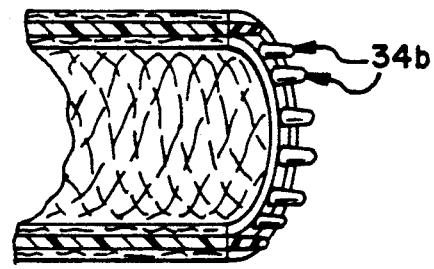
FIG. 5 is a cut away perspective view similar to FIG. 4 and in which biodegradation prevention of the reinforcing sleeve component is further enhanced by applying a soft polymer to the ends of the polymeric ribbon or filament of the intermediate layer of the embodiment illustrated in FIG. 2.
Figure 6:
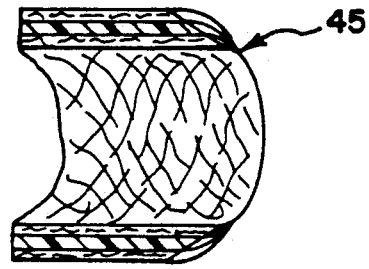
FIG. 6 is a cut away perspective view which illustrates another embodiment for preventing biodegradation of the reinforcing sleeve component of the embodiment illustrated in FIG. 2 by manicuring the ends of the polymeric ribbon or filament of the intermediate layer.

In order to enhance its resistance to biodegradation, the reinforcing sleeve component 20 may be given an atraumatic shape. With reference to FIGS. 4 through 6, this may be accomplished by, for example, spinning a plurality of the fibers 44 which form external layer 41 and a plurality of the fibers 24 which form internal layer 21 beyond the ends 35 of the ribbon or filament 34 from which intermediate layer 31 is formed, thereby encapsulating or covering the ends of the intermediate layer 31 to form a surface 44a. Fibers 24 and fibers 44, which form internal layer 21 and form external layer 41, respectively and are spun beyond the ends of the intermediate layer 31, may be heated, as with the entire component 20 to form a surface 44a which is smooth. Alternatively or additionally, the reinforcing sleeve component 20 may be rendered atraumatic by applying a bead 34b of a soft polymer, such as silicone rubber, to the ends of the fibers exposed at the periphery, or by providing the reinforcing sleeve component 20 with a manicured end 45 such as by flaring, tailoring, solvent manicuring and the like. Generally, when these types of treatments are carried out on the reinforcing sleeve component 20 they are most advantageously carried out on the fibers 34 which form the intermediate polymeric ribbon or filament layer 31.

Figure 3:
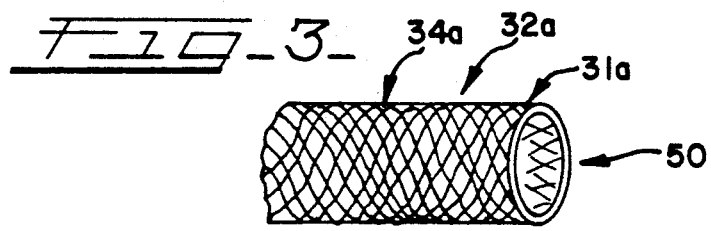
FIG. 3 is a perspective view, partially broken away, of another embodiment of a reinforcing sleeve component according to this invention into which the graft component illustrated in FIG. 1 may be fitted.

Another embodiment of the reinforcing sleeve component according to the present invention includes a single layer designated 50 in FIG. 3. The layer 50 may be fabricated by a suitable method such as that disclosed in U.S. Pat. No. 4,475,972 by winding fibers 34a, such as those made from a biocompatible material and about 1 micron to about 100 microns in diameter, onto a rotating mandrel at an angle within the range of about 75°±10° with respect to the common longitudinal axis of the mandrel. A generally noncompliant and very kink resistant tubular structure results. Upon completion of the winding, the reinforcing sleeve component 31a thus formed may be protected from biodegradation by suitable procedures or treatments.

A further embodiment of the reinforcing sleeve component according to the present invention is illustrated by the layer 50 in FIG. 3. In this embodiment, the layer 50 may be fabricated by a suitable method such as that disclosed in U.S. Pat. No. 4,475,972, from fibers 34a which are made from a biocompatible material having a relatively high durometer hardness that is greater than that of the fibers out of which graft component 31 is constructed. For example, graft component 31 can be made from Pellethane 80A polyurethane fibers, while the fibers 34a would be made of a harder material such as Pellethane 75D or Pellethane 55D polyurethane materials.

Fibers 34a of this further embodiment typically range from about 1 micron to about 100 microns in diameter and are wound onto a mandrel at an angle within the range of about 65°±20° with respect to the longitudinal axis of the mandrel. A relatively non-compliant, but very kink-resistant, tubular structure results. Upon completion of the winding, the reinforcing sleeve component 31a thus formed may be protected from biodegration by suitable treatments or other procedures.

A reinforced vascular graft according to the present invention may be formed by placing, such as sliding, any one of the embodiments of the reinforcing sleeve component over the graft component 11 to thereby form the reinforced graft assembly. The overall compliance of the reinforced graft may be controlled, to a certain degree, by the means used to join the two components, which may be accomplished during a surgical procedure. For example, if graft component 11 is held within the reinforcing sleeve component 20 or 50 by a friction fit, a relatively lesser compliant reinforced graft assembly will result. A more compliant reinforced graft assembly will result if the graft component 11 is loosely held within the reinforcing sleeve component 20 or 50 so that a spacing may be provided between the two components. Spacing would aid in the maintenance of the pulsatile flow through the assembly. The two components of a more compliant reinforced graft assembly may be fixed through the application of any appropriate fixative means, such as adhesives, for example, cyanoacrylate cement, fibrin glue, etc., or mechanical means, for example, sutures, velcro strips, etc. to one or both ends of the two components.

Accordingly, the compliance of the reinforced graft assembly of the present invention is adjustable in various ways. One can control the angle at which the fibers, that form either or both of the components, especially the sleeve, are wound. Generally, the greater the winding angle with respect to the longitudinal axis of the mandrel, the less compliant the graft. One can use fibers of differing hardness. One can use multiple layers to form the reinforcing sleeve component. Compliance of the reinforced graft assembly is also controlled by selecting the means used to join the two components of the assembly. For example, using a few interrupted sutures to secure the assembly together would maintain superior compliance. Additionally, by providing spacing between the two components, a more compliant assembly results.

It will be understood that the embodiments of the present invention as described are illustrative of some of the applications of the principles of the present invention. Modifications may be made by those skilled in the art without departure from the spirit and scope of the invention.

We claim:

1. A reinforced graft assembly, comprising:
   (a) a compliant graft component, said graft component having an inner surface and an outer surface, said graft component being made from synthetic, biologic, or biosynthetic materials; and
   (b) a sleeve component, said sleeve component being made from synthetic, biologic, or biosynthetic materials, said sleeve component being cylindrically shaped and having an inner diameter suitably sized so the sleeve component may be fitted over the graft component, whereby said sleeve component provides compliant reinforcement to said graft component, said sleeve component including layers which provide said reinforcement to said graft component, said layers including an internal layer, an intermediate layer, and an external layer, and wherein said intermediate layer includes fibers in the form of a ribbon or filament having a diameter in the range of 300 to 3,000 microns.

2. The reinforced graft assembly according to claim 1, wherein said internal layer includes fibers having a diameter in the range of 1 micron to 100 microns.

3. The reinforced graft assembly according to claim 1, wherein said external layer includes fibers having a diameter in the range of 1 micron to 100 microns.

4. The reinforced graft assembly according to claim 1, wherein said internal layer, said intermediate layer, and said external layer include fibers.

5. The reinforced graft assembly according to claim 4, wherein said intermediate layer fibers are at an angle in a range of 35° to 85° to the longitudinal axis of said sleeve component.

6. The reinforced graft assembly according to claim 1, wherein said fibers of said internal layer are made from polymeric material integrally bonded together.

7. The reinforced graft assembly according to claim 1, wherein said ribbon or filament of said intermediate layer is made from polymeric material integrally bonded together.

8. The reinforced graft assembly according to claim 3, wherein said fibers of said external layer are polymeric fibers which are integrally bonded together.

9. The reinforced graft assembly according to claim 1, wherein said internal layer includes a plurality of fibers and aid external layer includes a plurality of fibers spun longitudinally outward from ends of said ribbon or said filament from which said intermediate layer is formed to aid in protection of said sleeve component from biodegradation.

10. The reinforced graft assembly according to claim 1, wherein said sleeve component includes a soft polymer applied to ends of fibers from which said sleeve component is formed to aid in protection of said assembly from biodegradation.

11. The reinforced graft assembly according to claim 1, wherein said sleeve component includes manicured ends to aid in protection of said assembly from biodegradation.

* * * * *

UNITED STATES PATENT AND TRADEMARK OFFICE
CERTIFICATE OF CORRECTION

PATENT NO. : 5,084,065
DATED : January 28, 1992
INVENTOR(S) : Norman R. Weldon and David C. MacGregor It is certified that error appears in the above-indentified patent and that said Letters Patent is hereby corrected as shown below:

Col. 2, line 64, "bodies such" should read --bodies, such--.
Col. 8, line 28, "aid" should read --said--.

Signed and Sealed this

Eighteenth Day of October, 1994

Attest:

BRUCE LEHMAN

Attesting Officer

Commissioner of Patents and Trademarks